(12) United States Patent
Dyer et al.

(10) Patent No.: US 11,666,387 B2
(45) Date of Patent: *Jun. 6, 2023

(54) SYSTEM AND METHODS FOR AUTOMATIC MUSCLE MOVEMENT DETECTION

(71) Applicant: SYNAPTIVE MEDICAL INC., Toronto (CA)

(72) Inventors: Kelly Noel Dyer, Toronto (CA); Gal Sela, Toronto (CA); Kirusha Srimohanarajah, Toronto (CA); Sean Jy-Shyang Chen, Toronto (CA); Joshua Lee Richmond, Toronto (CA); Fergal Kerins, Toronto (CA)

(73) Assignee: Synaptive Medical Inc.

( * ) Notice: Subject to any disclaimer, the term of this patent is extended or adjusted under 35 U.S.C. 154(b) by 148 days.

This patent is subject to a terminal disclaimer.

(21) Appl. No.: 17/195,842

(22) Filed: Mar. 9, 2021

(65) Prior Publication Data

US 2021/0186628 A1 Jun. 24, 2021

Related U.S. Application Data

(63) Continuation of application No. 16/068,807, filed as application No. PCT/CA2016/050190 on Feb. 25, 2016, now Pat. No. 11,026,753.

(51) Int. Cl.
*A61B 34/20* (2016.01)
*A61B 90/00* (2016.01)
*A61B 90/14* (2016.01)

(52) U.S. Cl.
CPC .............. *A61B 34/20* (2016.02); *A61B 90/14* (2016.02); *A61B 2034/2055* (2016.02);
(Continued)

(58) Field of Classification Search
CPC . A61B 34/20; A61B 90/14; A61B 2043/2055; A61B 2043/2065;
(Continued)

(56) References Cited

U.S. PATENT DOCUMENTS

2004/0122311 A1* 6/2004 Cosman ................. A61B 90/14
600/427
2010/0067660 A1* 3/2010 Maurer, Jr. ............ A61B 6/486
378/95
(Continued)

FOREIGN PATENT DOCUMENTS

WO WO-2013180773 A1 * 12/2013 ......... A61B 1/00009
WO WO-2014139023 A1 * 9/2014 ......... A61B 17/3421
WO WO-2014173949 A1 * 10/2014 ............ A61B 3/113

*Primary Examiner* — Boniface Ngathi N

(57) ABSTRACT

A medical navigation system is provided for detecting movement of a subject, the system having an optical tracking system including a camera, a display, and a controller electrically coupled with the optical tracking system and the display. The controller has a processor coupled with a memory and is configured to receive a data signal from the optical tracking system and recognize and continuously monitor optical tracking markers on the subject within a field of view of the camera, and provide an alert on the display when movement of the optical tracking markers on the subject falls within predefined parameters.

20 Claims, 11 Drawing Sheets

(52) U.S. Cl.
CPC . *A61B 2034/2065* (2016.02); *A61B 2090/373* (2016.02); *A61B 2090/3735* (2016.02); *A61B 2090/3937* (2016.02)

(58) Field of Classification Search
CPC ...... A61B 2090/373; A61B 2090/3735; A61B 2090/3937
See application file for complete search history.

(56) References Cited

U.S. PATENT DOCUMENTS

| | | | |
|---|---|---|---|
| 2013/0345718 A1* | 12/2013 | Crawford | A61B 34/74 606/130 |
| 2015/0327948 A1* | 11/2015 | Schoepp | A61B 5/061 600/424 |
| 2021/0210837 A1* | 7/2021 | Hsu | H01Q 1/42 |

* cited by examiner

SYSTEM AND METHODS FOR AUTOMATIC MUSCLE MOVEMENT DETECTION

CROSS-REFERENCE TO RELATED APPLICATION(S)

This document is a continuation application, claiming the benefit of, and priority to the following application(s): U.S. patent application Ser. No. 16/068,807, filed on Jul. 9, 2018, and entitled "SYSTEM AND METHOD FOR AUTOMATIC MUSCLE MOVEMENT DETECTION," which is a National Stage application of International PCT Patent Application No. PCT/CA2016/050190 filed on Feb. 25, 2016, which are hereby incorporated by reference in their entirety.

FIELD

The present disclosure generally relates to image guided medical procedures and more specifically relates to a system and methods for automatic detection of muscle movement.

BACKGROUND

Related image guided medical procedures use a surgical instrument, such as an optical scope, an optical coherence tomography (OCT) probe, a micro ultrasound transducer, an electronic sensor or stimulator, or an access port based surgery. In the example of a port-based surgery, a surgeon or robotic surgical system may perform a surgical procedure involving tumor resection in which the residual tumor remaining after is minimized, while also minimizing the trauma to the intact white and grey matter of the brain. However, in such procedures, trauma may occur, for example, due to contact with the access port, stress to the brain matter, unintentional impact with surgical devices, and/or accidental resection of healthy tissue. A key to minimizing trauma is ensuring that the surgeon is aware of what is transpiring in the operating room and observes important signs when performing surgery such as patient muscle twitches or tremors.

Conventional systems have not offered good solutions for ensuring that a surgeon sees all of the reactions of a patient during the performance of a medical procedure. Therefore, a need exists for a system and methods that assist a surgeon in detecting changes in facial pose or other muscle positions to detect an onset of a seizure, muscle twitching, etc., thereby assisting the surgeon with clinical decision making in the context of the procedures mentioned above.

SUMMARY

One aspect of the present disclosure provides a medical navigation system for detecting movement of a subject, the system having an optical tracking system including a camera, a display, and a controller electrically coupled with the optical tracking system and the display. The controller has a processor coupled with a memory and is configured to: receive a data signal from the optical tracking system, recognize and continuously monitor optical tracking markers on the subject within a field of view of the camera, and provide an alert on the display when movement of the optical tracking markers on the subject falls within predefined parameters.

Another aspect of the present disclosure provides a medical navigation system for detecting movement of a subject, the system having a video system including a camera, a display, and a controller electrically coupled with the video system and the display. The controller has a processor coupled with a memory and is configured to: receive a data signal from the video system, recognize and continuously monitor a portion of the subject within a field of view of the camera, and provide an alert on the display when movement of the portion of the subject falls within predefined parameters.

Another aspect of the present disclosure provides a medical navigation system for detecting movement of a subject, the system having a three dimensional (3D) scanner system including a 3D scanner, a display, and a controller electrically coupled with the 3D scanner system and the display. The controller has a processor coupled with a memory and is configured to: receive a data signal from the 3D scanner system, recognize and continuously monitor a portion of the subject within a field of view of the 3D scanner, and provide an alert on the display when movement of the portion of the subject falls within predefined parameters.

A further understanding of the functional and advantageous aspects of the disclosure can be realized by reference to the following detailed description and the several figures of the drawings.

BRIEF DESCRIPTION OF THE DRAWINGS

Embodiments are described, by way of example only, with reference to the several figures of the drawings, in which.

DETAILED DESCRIPTION

Figure 1:
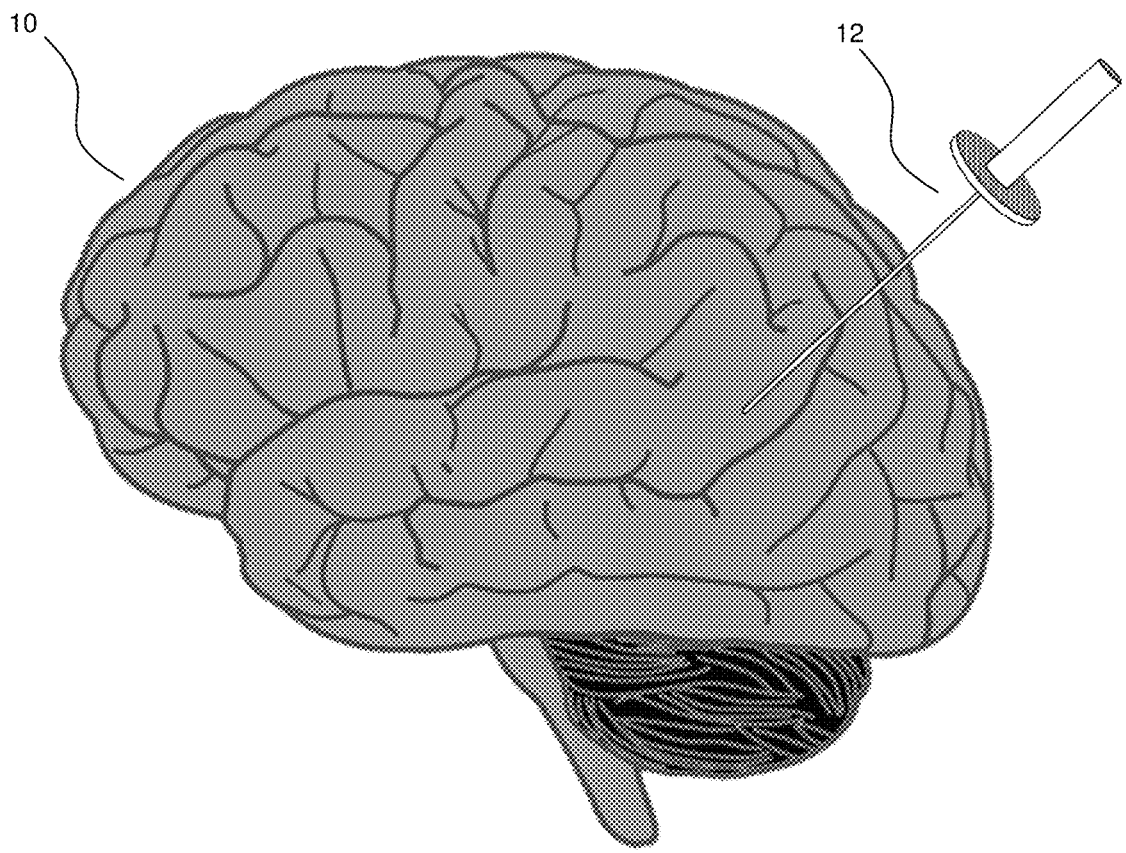
FIG. 1 is a diagram illustrating the insertion of an access port into a human brain, for providing access to internal brain tissue during a medical procedure.

Various embodiments and aspects of the disclosure will be described with reference to details below discussed. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and the claims, the terms, "comprises," "comprising," and variations thereof mean the specified features, steps or components are included. These terms are not to be interpreted to exclude the presence of other features, steps, or components.

As used herein, the term "exemplary" means "serving as an example, instance, or illustration," and should not be construed as preferred or advantageous over other configurations disclosed herein.

As used herein, the terms "about," "approximately," and "substantially" are meant to cover variations that may exist in the upper and lower limits of the ranges of values, such as variations in properties, parameters, and dimensions. In one non-limiting example, the terms "about," "approximately," and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings.

As used herein, the phrase "access port" refers to a cannula, conduit, sheath, port, tube, or other structure that is insertable into a subject in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event, or step that occurs, or is carried out, during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures, e g, minimally invasive medical procedures, are performed based on access to internal tissue through the access port.

Referring to FIG. 1, this diagram illustrates the insertion of an access port 12 into a human brain 10, for providing access to internal brain tissue during a medical procedure, in accordance with an embodiment of the present disclosure. The access port 12 is inserted into the human brain 10, providing access to internal brain tissue. Access port 12 may include such instruments as catheters, surgical probes, or cylindrical ports such as the NICO® BrainPath®. Surgical tools and instruments may then be inserted within the lumen of the access port in order to perform surgical, diagnostic or therapeutic procedures, such as resecting tumors as necessary. The present disclosure applies equally well to catheters, deep brain stimulation (DBS) needles, a biopsy procedure, and also to biopsies and/or catheters in other medical procedures performed on other parts of the body.

Still referring to FIG. 1, in the example of a port-based surgery, a straight or linear access port 12 is typically guided down a sulci path of the brain. Surgical instruments would then be inserted down the access port 12. Optical tracking systems, used in the medical procedure, track the position of a part of the instrument that is within line-of-site of the optical tracking camera.

Figure 2:
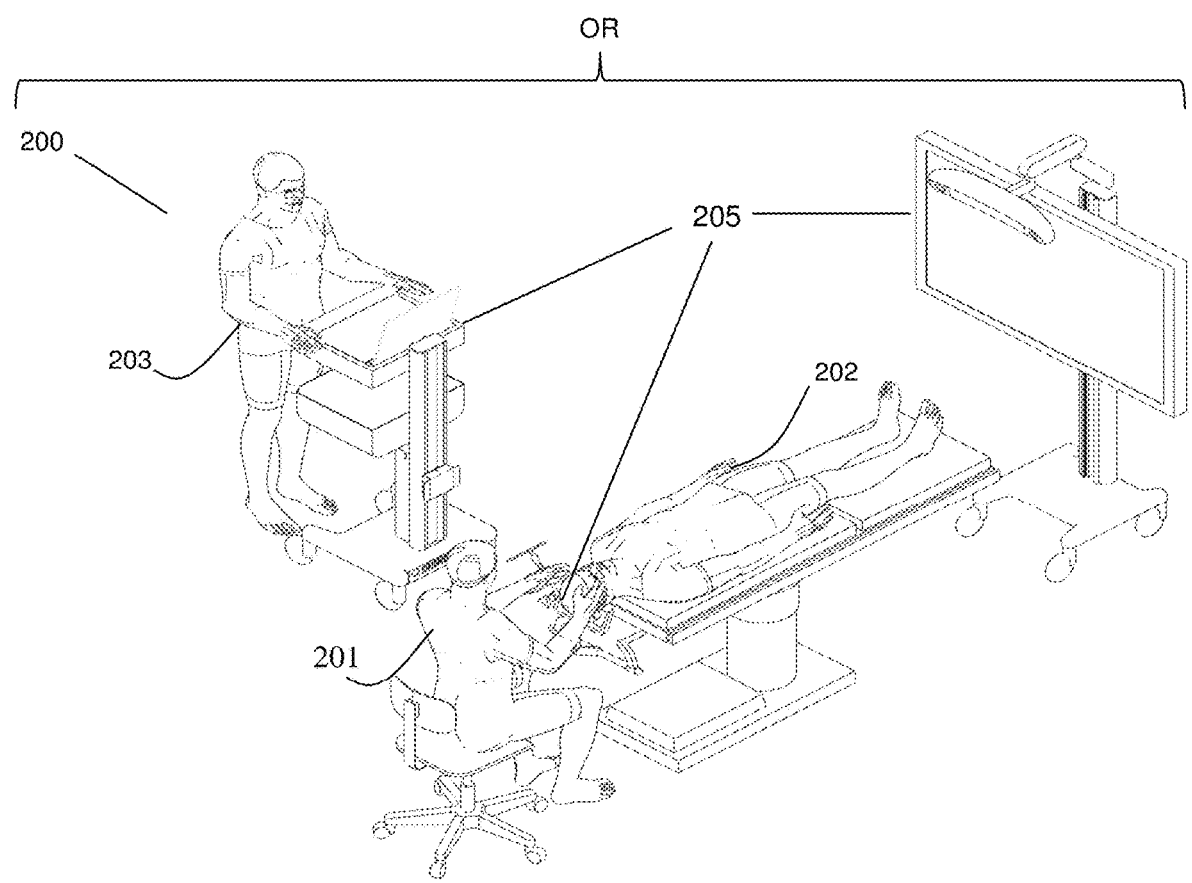
FIG. 2 is a diagram illustrating an exemplary navigation system for supporting minimally invasive surgery in an operating room.

Referring to FIG. 2, this diagram illustrates an exemplary navigation system environment 200 usable to support navigated image-guided surgery, in accordance with an embodiment of the present disclosure. The surgeon 201 conducts a surgery on a patient 202 in an operating room OR environment. A medical navigation system 205, comprising an equipment tower, tracking system, displays, and tracked instruments assist the surgeon 201 during his procedure. An operator 203 is also present to operate, control, and provide assistance for the medical navigation system 205.

Figure 3:
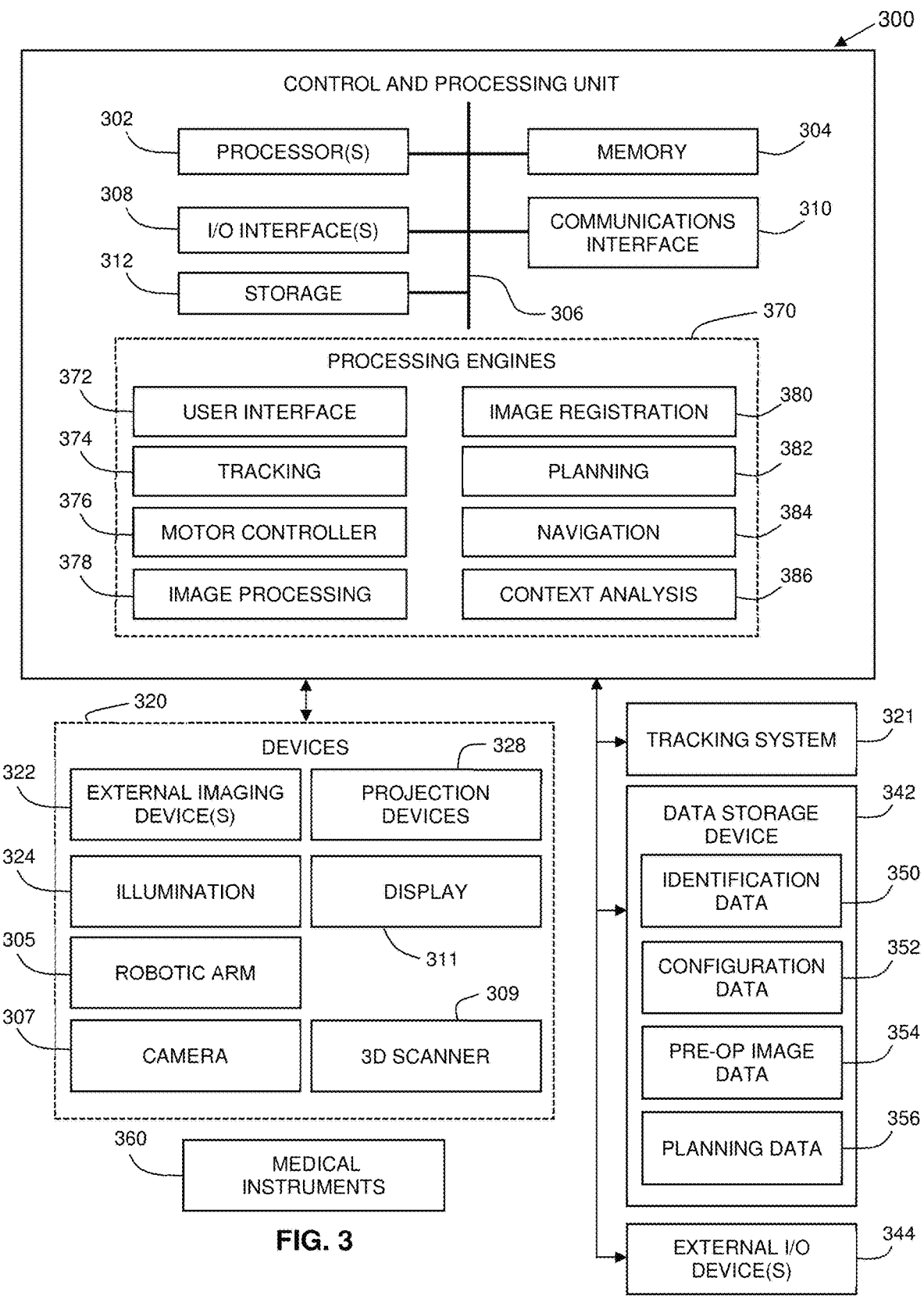
FIG. 3 is a block diagram illustrating a control and processing system, as shown in FIG. 2, that usable in the navigation system.

Referring to FIG. 3, this block diagram illustrates a control and processing system 300 usable in the medical navigation system 200, as shown in FIG. 2, e.g., as part of the equipment tower. In one example, the control and processing system 300 comprises one or more processors 302, a memory 304, a system bus 306, one or more input/output interfaces 308, a communications interface 310, and a storage device 312. Control and processing system 300 is interfaced with other external devices, such as a tracking system 321, a data storage 342, and external user input and output devices 344. The external user input and output devices 344 comprise, for example, one or more of a display, a keyboard, a mouse, sensors attached to medical equipment, a foot pedal, a microphone, and a speaker. Data storage 342 comprises any suitable data storage device, such as a local or remote computing device, e.g., a computer, hard drive, digital media device, or server, having a database stored thereon. In the example shown, data storage device 342 comprises identification data 350 for identifying one or more medical instruments 360 and configuration data 352 that associates customized configuration parameters with one or more medical instruments 360. Data storage device 342 comprises preoperative image data 354 and/or medical procedure planning data 356. Although data storage device 342 is shown as comprising a single device, understood is that, in other embodiments, data storage device 342 comprises multiple storage devices.

Still referring to FIG. 3, the medical instruments 360 are identifiable by control and processing unit 300. Medical instruments 360 are coupled with, and controlled by, the control and processing unit 300. Alternatively, the medical instruments 360 are operated, or otherwise employed, independent of the control and processing unit 300. Tracking system 321 is employed to track one or more of medical instruments 360 and to spatially register the one or more tracked medical instruments to an intraoperative reference frame. For example, medical instruments 360 comprise tracking markers, such as tracking spheres recognizable by a tracking camera 307. In one example, the tracking camera 307 comprises an infrared (IR) tracking camera. In another example, a sheath placed over a medical instrument 360 and is coupled with, and controlled by, the control and processing unit 300. In another example, the tracking camera 307 comprises a video camera.

Still referring to FIG. 3, the control and processing unit 300 interfaces with a number of configurable devices, and intraoperatively reconfigures one or more of such devices based on configuration parameters obtained from configuration data 352. Examples of devices 320 include one or more external imaging devices 322, one or more illumination devices 324, a robotic arm 305, one or more projection devices 328, and one or more displays 311, and a scanner 309, which in one example may be a three dimensional (3D) scanner.

Still referring to FIG. 3, exemplary aspects of the disclosure are implemented via processor(s) 302 and/or memory 304. For example, the functionalities, described herein, are partially implemented via hardware logic in processor 302 and are partially implemented using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately, in one example, the processing modules 370 are stored in the memory 304; and the processing modules are collectively referred to as processing modules 370.

Still referring to FIG. 3, understood is that the system is not intended to be limited to the components shown. One or more components of the control and processing system 300 may be provided as an external component or device. In one example, navigation module 384 may be provided as an external navigation system that is integrated with control and processing system 300.

Still referring to FIG. 3, some embodiments are implemented using processor 302 without additional instructions stored in memory 304. Some embodiments are implemented using the instructions stored in memory 304 for execution by one or more general purpose microprocessors. Thus, the present disclosure is not limited to a specific configuration of hardware and/or software.

While some embodiments can be implemented in fully functioning computers and computer systems, various embodiments are capable of being distributed as a computing product in a variety of forms and are capable of being applied, regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache, or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc., among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, universal serial bus (USB) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present disclosure, the navigation system 205, comprising the control and processing unit 300, provide tools to the neurosurgeon that will lead to the most informed, least damaging, neurosurgical operations. In addition to removal of brain tumours and intracranial hemorrhages (ICH), the navigation system 205 is also applied to a brain biopsy, a functional/deep-brain stimulation, a catheter/shunt placement procedure, open craniotomies, endonasal/skull-based/ear nose throat (ENT), spine procedures, and other parts of the body, such as breast biopsies, liver biopsies, etc. While several examples have been provided, aspects of the present disclosure may be applied to any suitable medical procedure.

Figure 4A:
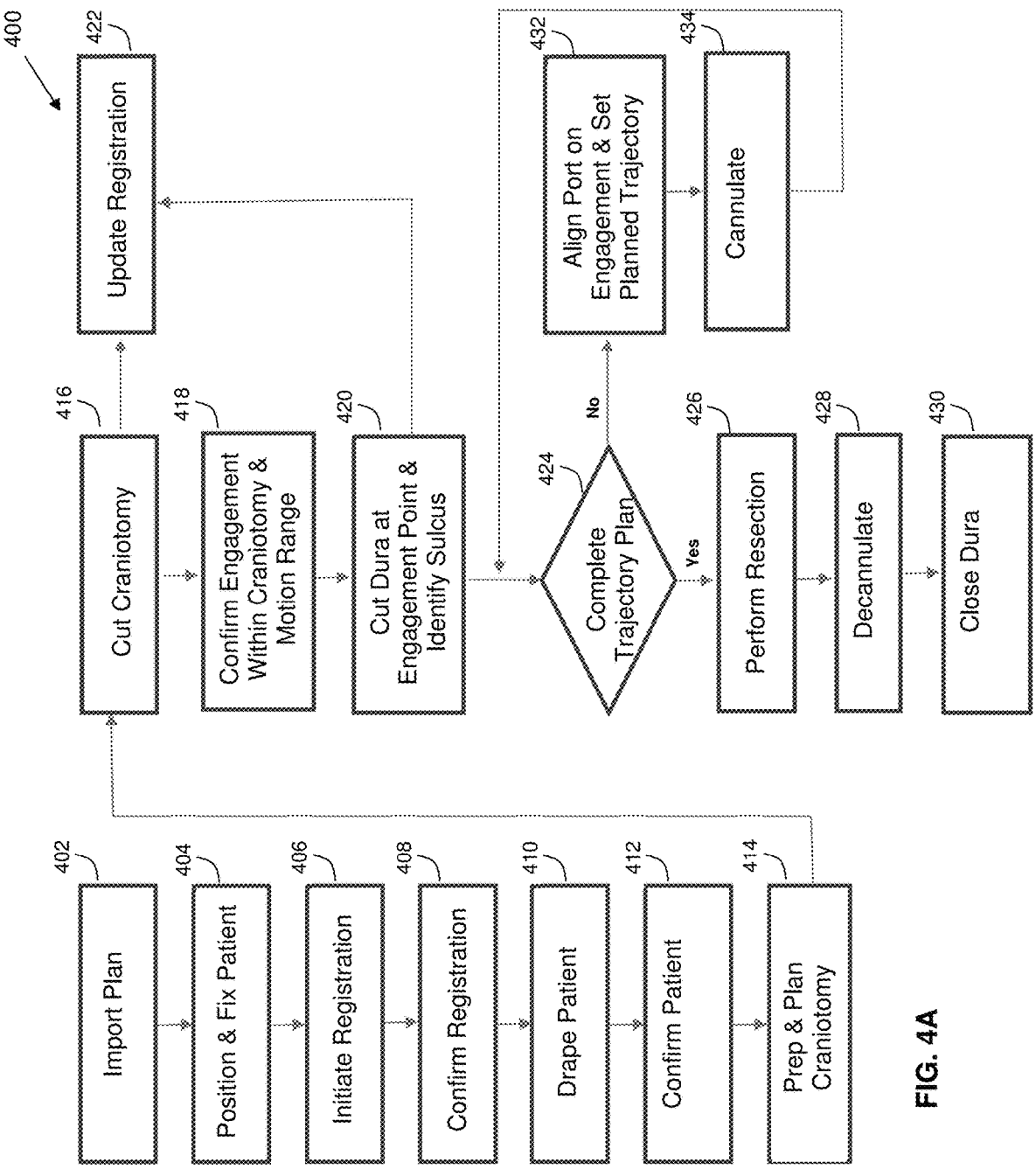
FIG. 4A is a flow chart illustrating a method involved in a surgical procedure using the navigation system, as shown in FIG. 2.

Referring to FIG. 4A, this flow chart illustrates a method 400 of performing a surgical procedure using a navigation system, such as the medical navigation system 205, as shown in FIG. 2, in accordance with an embodiment of the present disclosure. At a first block 402, the surgical plan is imported.

Still referring to FIG. 4A, once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower of medical navigation system 205.

Still referring to FIG. 4A, next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Appreciated is that numerous registration techniques are available; and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space.

Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
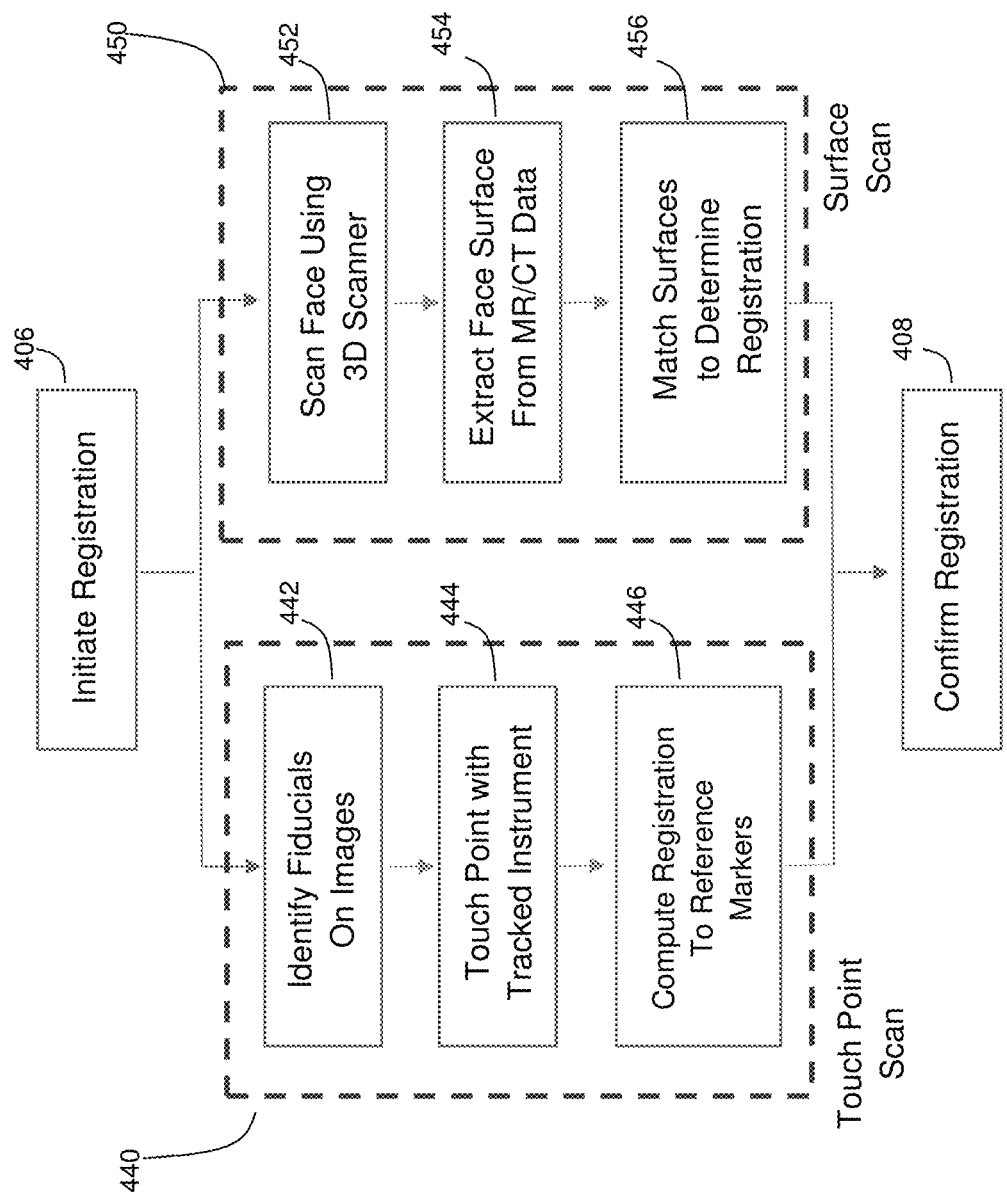
FIG. 4B is a flow chart illustrating a method of registering a patient for a surgical procedure, as shown in FIG. 4A.

Referring now to FIG. 4B, this flow chart illustrates a method involved in registration block 406, as shown in FIG. 4A, in greater detail, in accordance with an embodiment of the present disclosure. If the use of fiducial touch points (block 440) is contemplated, the method involves first identifying fiducials on images (block 442), then touching the touch points with a tracked instrument (block 444). Next, the navigation system computes the registration to reference markers (block 446).

Still referring now to FIG. 4B, alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456). Upon completion of either the fiducial touch points (block 440) or surface scan (block 450) procedures, the data extracted is computed and used to confirm registration at block 408.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms, e.g., bacteria, between non-sterile and sterile areas. At this point, conventional navigation systems require that the non-sterile patient reference is replaced with a sterile patient reference of identical geometry location and orientation.

Still referring back to FIG. 4A, upon completion of draping (block 410), the patient engagement points are confirmed (block 412) and then the craniotomy is prepared and planned (block 414). Upon completion of the preparation and planning of the craniotomy (block 414), the craniotomy is cut and a bone flap is temporarily removed from the skull to access the brain (block 416). Registration data is updated with the navigation system at this point (block 422). Next, the engagement within craniotomy and the motion range are confirmed (block 418). Next, the procedure advances to cutting the dura at the engagement points and identifying the sulcus (block 420).

Still referring back to FIG. 4A, thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Still referring back to FIG. 4A, once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of the method 400, as shown in FIG. 4A, are specific to port-based surgery, such as portions of blocks 428, 420, and 434, but the appropriate portions of these blocks may be skipped or suitably modified when performing non-port based surgery.

Referring back to FIGS. 4A and 4B, together, when performing a surgical procedure using a medical navigation system 205, the medical navigation system 205 must acquire and maintain a reference of the location of the tools in use as well as the patient in three dimensional (3D) space. In other words, during a navigated neurosurgery, there needs to be a tracked reference frame that is fixed relative to the patient's skull. During the registration phase of a navigated neurosurgery, e.g., the step 406 shown in FIGS. 4A and 4B, a transformation is calculated that maps the frame of reference of preoperative MRI or CT imagery to the physical space of the surgery, specifically the patient's head. This may be accomplished by the navigation system 205 tracking locations of fiducial markers fixed to the patient's head, relative to the static patient reference frame. The patient reference frame is typically rigidly attached to the head fixation device, such as a Mayfield clamp. Registration is typically performed before the sterile field has been established, e.g., the step 410 (FIG. 4A).

Figure 5:
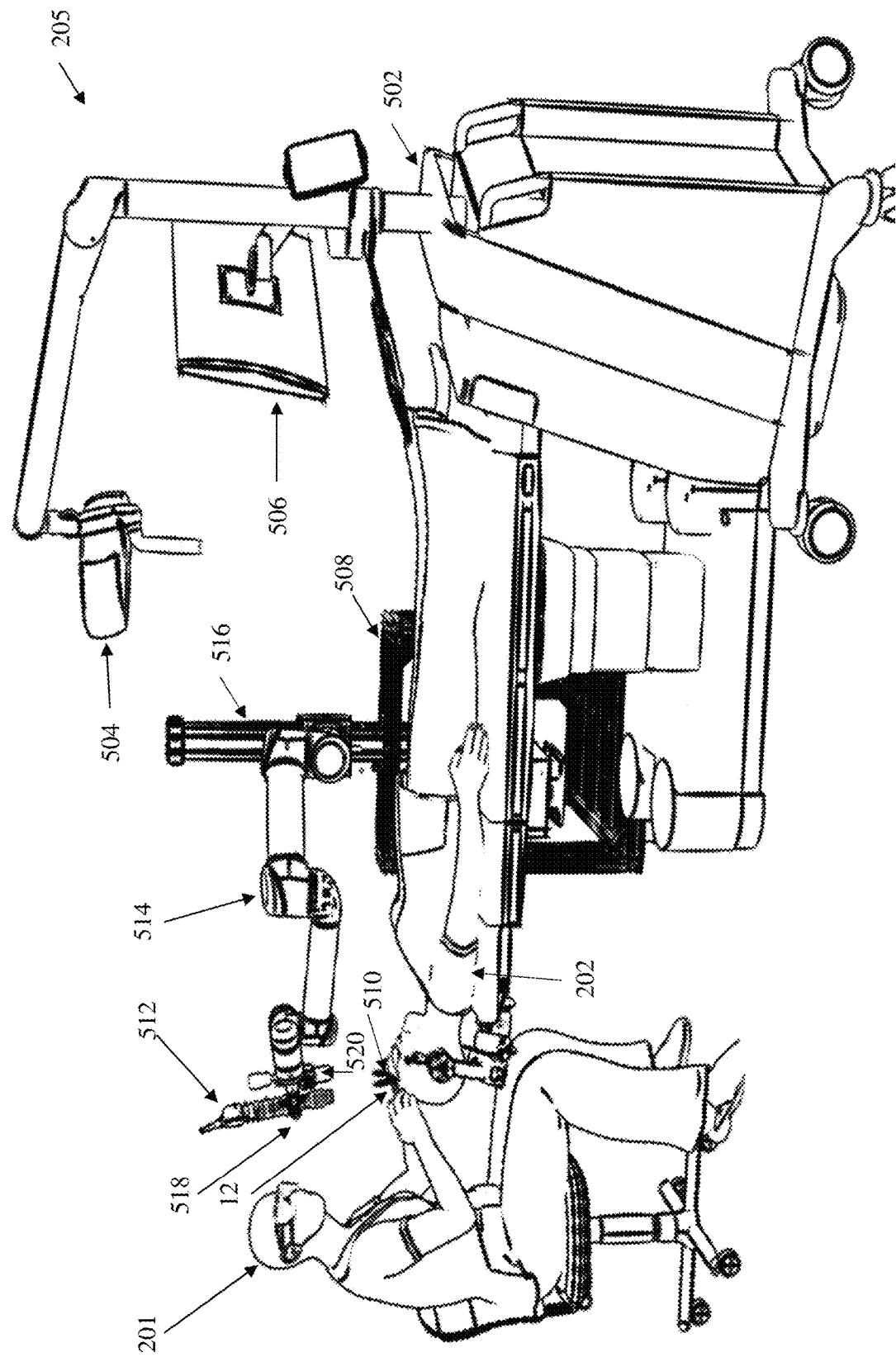
FIG. 5 is a diagram illustrating an exemplary navigation system, as shown in FIG. 2, comprising system components of an exemplary surgical system usable for automatic muscle movement detection.

Referring to FIG. 5, this diagram illustrates components of an exemplary surgical system as shown in FIG. 2, in accordance with an embodiment of the present disclosure. The navigation system 205 comprises an equipment tower 502, tracking system 504, display 506, an intelligent positioning system 508, and tracking markers 510 used to tracked instruments or an access port 12. Tracking system 504 may also comprise an optical tracking device, tracking camera, video camera, 3D scanner, or any other suitable camera of scanner based system. The surgeon 201 performs a tumor resection through a port 12, using an imaging device 512, e.g., a scope and camera, to view down the port at a sufficient magnification to enable enhanced visibility of the instruments and tissue. The imaging device 512 comprises an external scope, videoscope, wide field camera, or an alternate image capturing device. The imaging sensor view is depicted on the visual display 506 which the surgeon 201 uses for navigating the port's distal end through the anatomical region of interest.

Still referring to FIG. 5, an intelligent positioning system 508 comprising an automated arm 514, a lifting column 516 and an end effector 518, is placed in proximity to patient 202. Lifting column 516 is connected to a frame of intelligent positioning system 508. The proximal end of automated mechanical arm 514 (further known as automated arm 514 herein) is coupled with the lifting column 516. In other embodiments, the automated arm 514 may be connected to a horizontal beam, which is then either connected to lifting column 516 or directly to frame of the intelligent positioning system 508. Automated arm 514 may have multiple joints to enable 5, 6 or 7 degrees of freedom.

Still referring to FIG. 5, end effector 518 is attached to the distal end of automated arm 514. End effector 518 may accommodate a plurality of instruments or tools that may assist surgeon 201 in his procedure. End effector 518 is shown as holding an external scope and camera, however it should be noted that this is merely an example and alternate devices may be used with the end effector 518, such as a wide field camera, microscope and OCT (Optical Coherence Tomography), video camera, 3D scanner, or other imaging instruments. In another example, multiple end effectors may be attached to the distal end of automated arm 518, and, thus, assist the surgeon 201 in switching between multiple modalities. For example, the surgeon 201 may want the ability to move between microscope, and OCT with stand-off optics. In a further example, the ability to attach a second, more accurate, but smaller range end effector such as a laser based ablation system with micro-control may be contemplated.

Still referring to FIG. 5, in one example, the intelligent positioning system 508 receives as input the spatial position and pose data of the automated arm 514 and target (for example the port 12) as determined by tracking system 504 by detection of the tracking markers on the wide field camera on port 12. Further, it should be noted that the tracking markers may be used to track both the automated arm 514 as well as the end effector 518 either collectively or independently. A wide field camera 520 is coupled with the external scope, e.g., imaging device 512; and the two imaging devices, together, are held by the end effector 518. Although these two imaging devices are depicted together for illustration, either imaging device could be utilized independently of the other imaging device, for example, wherein an external video scope is used independently of the wide field camera 520.

Still referring to FIG. 5, intelligent positioning system 508 computes the desired joint positions for automated arm 514 so as to maneuver the end effector 518 mounted on the automated arm's distal end to a predetermined spatial position and pose relative to the port 12. This redetermined relative spatial position and pose is termed the "Zero Position," wherein the sensor of imaging device 512 and port 12 are axially aligned.

Still referring to FIG. 5, further, the intelligent positioning system 508, optical tracking device 504, automated arm 514, and tracking markers 510 may form a feedback loop to maintain the distal end of the port 12 (located inside the brain) in constant view and focus of the end effector 518, given that the optical tracking device 504 is an imaging device as the port position may be dynamically manipulated by the surgeon during the procedure. Intelligent positioning system 508 may also include a foot pedal for use by the surgeon 201 to align the end effector 518, e.g., holding a videoscope, of automated arm 514 with the port 12.

Figure 6:
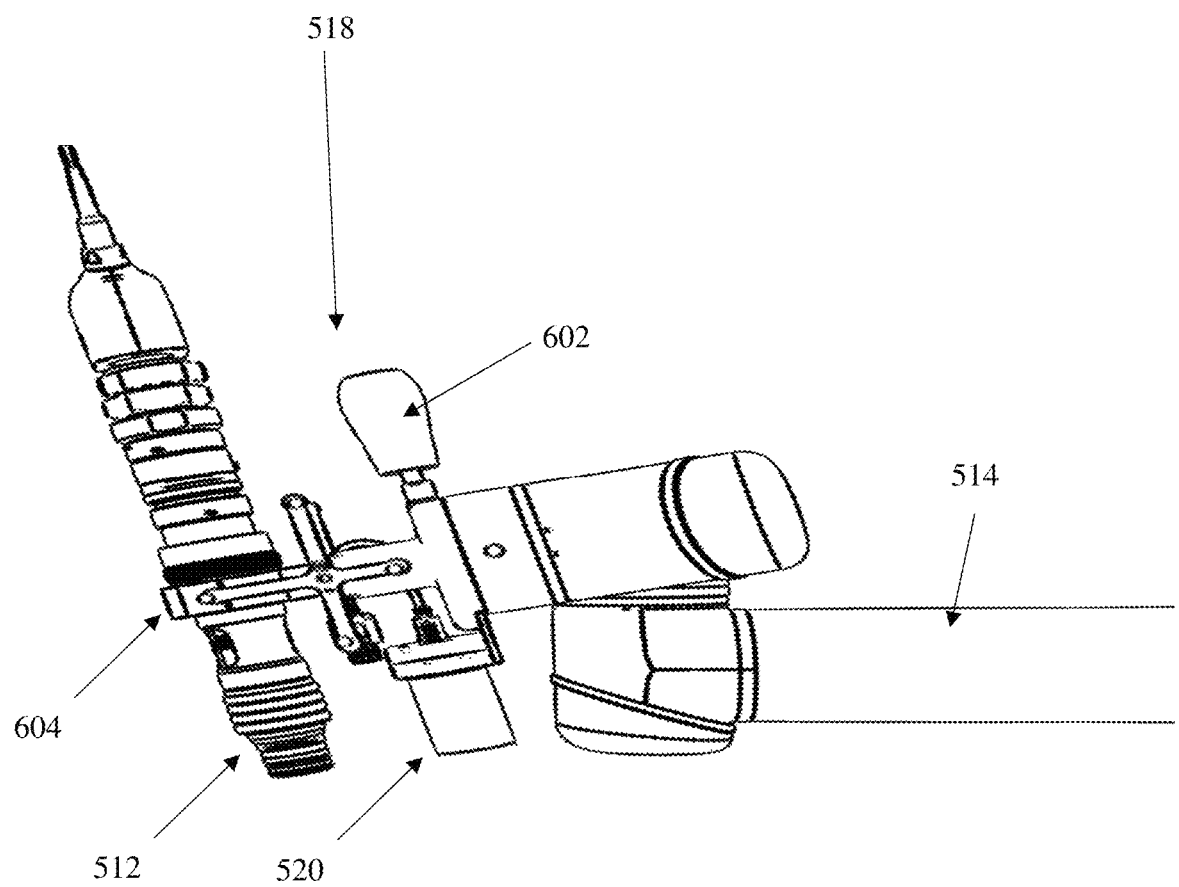
FIG. 6 is diagram illustrating, in a perspective view, a conventional end effector holding a camera.

Referring to FIG. 6, this diagram illustrates an end effector 518 is shown attached to automated arm 514, in accordance with an embodiment of the present disclosure. The end effector 518 comprises a handle 602 and a scope clamp 604. The scope clamp 604 holds imaging device 512. The end effector also has wide field camera 520 attached thereto, which, in one example, comprises a still camera, video camera, or a 3D scanner used to monitor muscles of the patient for movement, tremors, or twitching.

Figure 7:
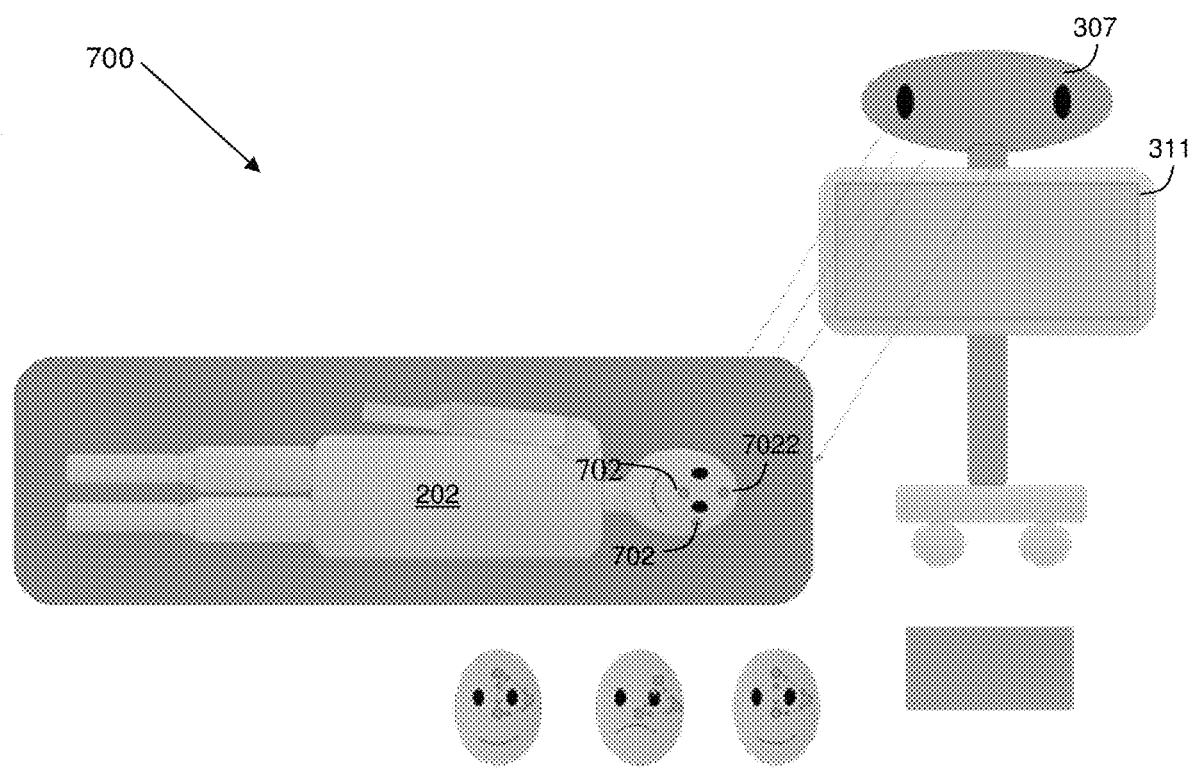
FIG. 7 is a diagram illustrating an exemplary patient context in an operating room where automatic muscle movement detection is provided.

Referring to FIG. 7, this block diagram illustrates an exemplary patient context 700 in an operating room OR where automatic muscle movement detection may be provided, in accordance with an embodiment of the present disclosure. A medical navigation system 205 is used for detecting movement of a subject, such as patient 202. The medical navigation system 205 comprises an optical tracking system including a camera 307, a display 311, and a controller 300, as shown in FIG. 3, electrically coupled with the optical tracking system and the display 311. The controller 300 comprises a processor, such as processor 302 (FIG. 3) coupled with a memory, such as the memory 304 (FIG. 3). The controller is configured to: receive a data signal from the camera 307 of the optical tracking system, recognize and continuously monitor optical tracking markers 702 on the subject within a field of view of the camera 307, and provide an alert on the display 311 when movement of the optical tracking markers 702 on the subject falls within predefined parameters.

Still referring to FIG. 7, the predefined parameters may include a muscle movement indicative of a patient event, a muscle twitch indicative of a patient event, a large muscle movement, or a muscle tremor indicative of a patient event. The patient event signifies a physiological state of the patient that is of concern. For example, certain muscle tremors that are observed on a patient might indicate that the patient is about to have a seizure. In another example, certain muscle twitches observed on the face of a patient during a brain surgery might be indicative that the surgeon is making contact with a portion of the brain of the patient where great care should be taken. When a surgeon is performing a procedure on the brain of the patient 202, important is that the surgeon is aware of the reaction of the patient to the procedure being performed. Muscle twitches or tremors are an important symptom of this reaction of which the surgeon should be aware. The medical navigation system 205 continuously, and/or automatically, monitors the patient 202 for muscle tremors or twitches and provides an alert to the surgeon when such a tremor or twitch is detected. In one example, the alert is provided on the display 311. In other examples, the alert is provided in the form of an audio alert or a vibratory alert.

Still referring to FIG. 7, in one example, each of the optical tracking markers 702 on the subject is identifiable by the medical navigation system 205 as unique. The optical tracking markers 702 comprise stickers disposed on the skin of the patient 202 and could differ from each other by shape, size, reflectivity, and/or color. While three optical tracking markers 702 are shown located on a face of the subject by way of example, any suitable number of optical tracking markers may be used such as two markers, three markers, four markers, five markers, or more. The tracking markers 702 may be located on any suitable body part such as on the face, on the fingers or toes, or even on the chest of the subject, depending which muscles the surgeon wishes to monitor for movement. Further, different types of optical tracking markers are used, such as active optical tracking markers, e.g., light emitting diodes (LEDs) or passive optical tracking markers. The configuration illustrated is particularly advantageous as no registration of the optical tracking markers 702 on the subject is needed prior to detecting the twitch or tremor and providing the alert.

Still referring to FIG. 7 and referring back to FIG. 3, in another example, a medical navigation system 205 is used for detecting movement of a subject, such as patient 202. The medical navigation system 205 comprises a video system, including a camera, such as a video camera, a display, such as display 311 (FIG. 3), and a controller, such as controller 300 (FIG. 3) electrically coupled with the video system and the display 311. The controller 300 comprises a processor, such as processor 302 (FIG. 3), coupled with a memory, such as memory 304 (FIG. 3). The controller is configured to: receive a data signal from the video camera of the video system, recognize and continuously monitor a portion of the subject within a field of view of the camera, and provide an alert on the display 311 when movement of the portion of the subject falls within predefined parameters. The video camera may be mounted in a position similar to that of camera 307. Alternatively, the video camera is mounted on an end effector, such as end effector 518 coupled with an intelligent positioning system 508, which allows the intelligent positioning system 508 to position the video camera in a suitable position for monitoring the appropriate muscles of the patient 202. Intelligent positioning system 508 may also automatically adjust the position of the video camera throughout the medical procedure, either to maintain the appropriate muscles within its field of view or to focus on different muscles when so directed by the surgeon, or both.

Still referring to FIG. 7 and referring back to FIGS. 2 and 3, when a video camera is used, instead of optical markers and an optical tracking system, the predefined parameters comprise a muscle movement indicative of a patient event, a muscle twitch indicative of a patient event, a large muscle movement, or a muscle tremor indicative of a patient event. The patient event signifies a physiological state of the patient that is of concern. For example, certain muscle tremors that are observed on a patient might indicate that the patient is about to have a seizure. In another example, certain muscle twitches observed on the face of a patient during a brain surgery might be indicative that the surgeon is making contact with a portion of the brain of the patient where great care should be taken. When a surgeon is performing a procedure on the brain of the patient 202, important is that the surgeon is aware of the reaction of the patient to the procedure being performed. Muscle twitches or tremors are an important symptom of this reaction of which the surgeon should be aware. The medical navigation system 205 continuously and/or automatically monitors the patient 202 for muscle tremors or twitches and provide an alert to the surgeon when such a tremor or twitch is detected. In one example, the alert may be provided on the display 311. In other examples, the alert may be provided in the form of an audio alert or a vibratory alert.

Still referring to FIG. 7 and referring back to FIGS. 2 and 3, in another example, a medical navigation system 205 is used for detecting movement of a subject, such as patient 202. The medical navigation system 205 comprises a three dimensional (3D) scanner system, including a 3D scanner, such as 3D scanner 309 (FIG. 3), a display, such as display 311 (FIG. 3), and a controller, such as controller 300 (FIG. 3), electrically coupled with the 3D scanner system and the display 311. The controller 300 comprises a processor, such as processor 302 (FIG. 3) coupled with a memory, such as memory 304 (FIG. 3). The controller is configured to: receive a data signal from the 3D scanner 309 of the 3D scanner system, recognize and continuously monitor a portion of the subject within a field of view of the 3D scanner 309, and provide an alert on the display 311 when movement of the portion of the subject falls within predefined parameters. The 3D scanner 309 is mounted in a position similar to that of camera 307. Alternatively, the 3D scanner 309 is mounted on an end effector, such as end effector 518 coupled with intelligent positioning system 508, which allows the intelligent positioning system 508 to position the 3D scanner 309 in a suitable position for monitoring the appropriate muscles of the patient 202. Intelligent positioning system 508 may also automatically adjust the position of the 3D scanner 309 throughout the medical procedure, either to maintain the appropriate muscles within its field of view or to focus on different muscles when so directed by the surgeon, or both.

Still referring to FIG. 7 and referring back to FIGS. 2 and 3, when a 3D scanner is used instead of optical markers and an optical tracking system, the predefined parameters comprise a muscle movement indicative of a patient event, a muscle twitch indicative of a patient event, a large muscle movement, or a muscle tremor indicative of a patient event. The patient event signifies a physiological state of the patient that is of concern. For example, certain muscle tremors that are observed on a patient might indicate that the patient is about to have a seizure. In another example, certain muscle twitches observed on the face of a patient during a brain surgery might be indicative that the surgeon is making contact with a portion of the brain of the patient where great care should be taken. When a surgeon is performing a procedure on the brain of the patient 202, important is that the surgeon is aware of the reaction of the patient to the procedure being performed. Muscle twitches or tremors are an important symptom of this reaction of which the surgeon should be aware. The medical navigation system 205 continuously and/or automatically monitors the patient 202 for muscle tremors or twitches and provides an alert to the surgeon when such a tremor or twitch is detected. In one example, the alert is provided on the display 311. In other examples, the alert is provided in the form of an audio alert or a vibratory alert.

Figure 8:
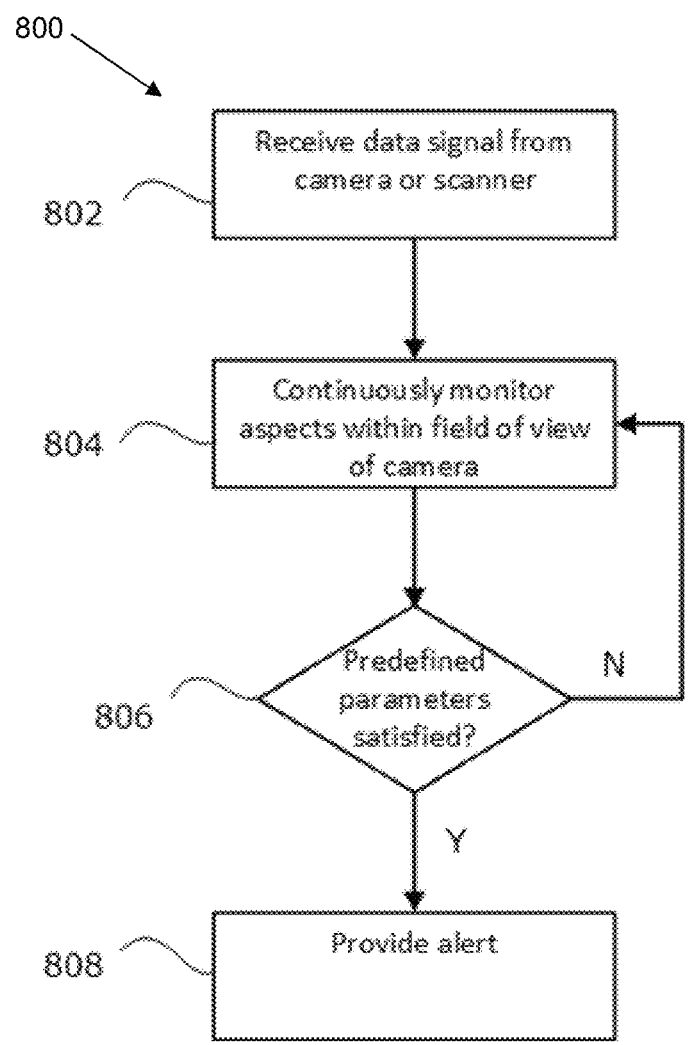
FIG. 8 is a flow chart illustrating a method of automatically detecting muscle movement implementable by the navigation system, as shown in FIGS. 5 and 7.

Referring now to FIG. 8 and referring back to FIGS. 2, 3, 5 and 7, this flow chart illustrating a method 800 of automatic muscle movement detection implemented by a medical navigation system 205, in accordance with an embodiment of the present disclosure. In one example, the method 800 is implemented by a controller, such as controller 300 (FIG. 3) comprising a processor, such as processor 302 (FIG. 3) coupled with a memory, such as memory 304 (FIG. 3) and a display 311.

Still referring now to FIG. 8 and referring back to FIGS. 2, 3, 5 and 7, at a first block 802, the controller 300 of the medical navigation system 205 receives a data signal from a camera or scanner. Depending on the particular implementation, the data signal is provided by an optical tracking system comprising a camera 307, a video camera, or a 3D scanner system including 3D scanner 309. Next, at a block 804, the controller 300 continuously monitors aspects within the field of view of the camera or scanner. Where an optical tracking system is used, the controller 300 monitors the tracking markers 702, which, in one example, may each be uniquely identifiable by the system 205 based on different shapes, sizes, reflectivities, or colors, and monitors the distances in between the tracking markers 702 relative to each other. A facial twitch would change the distances between the tracking markers 702, which provides the system 205 with data for analysis. In another example, where a video camera or 3D scanner system is used, the system 205 monitors facial features, muscle positions, or the positions of appendages or fingers or toes directly.

Still referring now to FIG. 8 and referring back to FIGS. 2, 3, 5 and 7, next, at a block 806, the controller 300 whether the predefined parameters have been satisfied. For example, in the case where an optical tracking system is used and the tracking markers 702 are being monitored, the controller 300 checks for changing distances between the tracking markers 702 relative to each other that meet predefined frequency and/or magnitude thresholds that would be indicative of a muscle twitch, tremor, or an impending seizure. In another example, where a video camera or 3D scanner system is used, the controller 300 monitors facial features, muscle positions, or the positions of appendages or fingers or toes directly and may also check frequency and/or magnitude thresholds of muscle movement that would be indicative of a muscle twitch, tremor, or an impending seizure. If muscle movement, tremors, or twitches are not detected that meet the predefined parameters, e.g., thresholds, then the method 800 returns to the block 804.

Still referring now to FIG. 8 and referring back to FIGS. 2, 3, 5 and 7, if muscle movement, tremors, or twitches are detected that meet the predefined parameters, e.g., thresholds, then the method 800 continues at the block 808 where an alert is provided to the surgeon. As described above, the alert could be in any suitable form, for example by way of a visual alert on the display 311, or by way of an auditory or vibratory alert.

Still referring now to FIG. 8 and referring back to FIGS. 2, 3, 5 and 7, some methods of twitch detection include detection of a twitch or facial gesture. A twitch or facial gesture is detected using cameras and 3D scanners. Facial movement is detected and analyzed using software methods and other techniques at a particular facial landmark. For example, a facial landmark comprises any one of an eye, an eyebrow, a mouth area, a forehead area, lips, cheeks and a nose or any combination thereof. A facial movement comprises any one of a blink gesture, a wink gesture, an ocular movement, a smile gesture, a frown gesture, a tongue protrusion gesture, an open mouth gesture, an eyebrow movement, a forehead wrinkle gesture, and a nose wrinkle gesture, or any combination thereof. Suitable methods for detecting facial gestures or movement comprise, for example in U.S. Pat. No. 8,457,367, the entirety of which is hereby incorporated by reference.

Still referring now to FIG. 8 and referring back to FIGS. 2, 3, 5 and 7, one method of detecting and differentiating a twitch from other facial movement comprises checking frequency and/or magnitude thresholds of muscle movement that could be indicative of a muscle twitch, tremor, or an impending seizure. Another method comprises using machine learning and facial analysis software such as Shore®, an object and facial recognition engine offered by Fraunhofer®, which trains the system by accessing a stored database of over 10000 annotated faces to provide high recognition rates. A further facial movement detection method may incorporate the use of neural networks, as described by Ma, L. and Khorasani, K., "Facial expression recognition using constructive feedforward neural networks." IEEE Systems, Man, and Cybernetics, Part B: Volume: 34, Issue: 3, (June 2004) pp. 1588-1595, the entirety of which is hereby incorporated by reference.

Still referring now to FIG. 8 and referring back to FIGS. 2, 3, 5 and 7, a further exemplary facial movement detection method is used, such as error-correcting output code (ECOC) Classifiers and Platt Scaling, as described by Smith, Raymond S. and Windeatt, Terry, "Facial Expression Detection using Filtered Local Binary Pattern Features with ECOC Classifiers and Platt Scaling" JMLR: Workshop and Conference Proceedings 11 (2010), pp. 111-118, the entirety of which is hereby incorporated by reference. While several examples of movement or twitch detection are provided that may be suitable for use in blocks 804-806 of method 800, any suitable method may be used according to a particular application.

Still referring now to FIG. 8 and referring back to FIGS. 2, 3, 5 and 7, in some examples, the system and method described herein is used to monitor patients in post-operative states of recovery who are potentially alone in a recovery room. The medical navigation system 205 could, at the block 808, send an alert to a central hospital monitoring system to provide an alert within the hospital or the alert could be sent directly to a health care professional, for example, by way of telephone call, text message, email message or other suitable communication to a smart phone or any other communication device. In another example, the system and method described herein could have applications in physiotherapy or in an intensive care unit where such monitoring could be advantageous.

Figure 9:
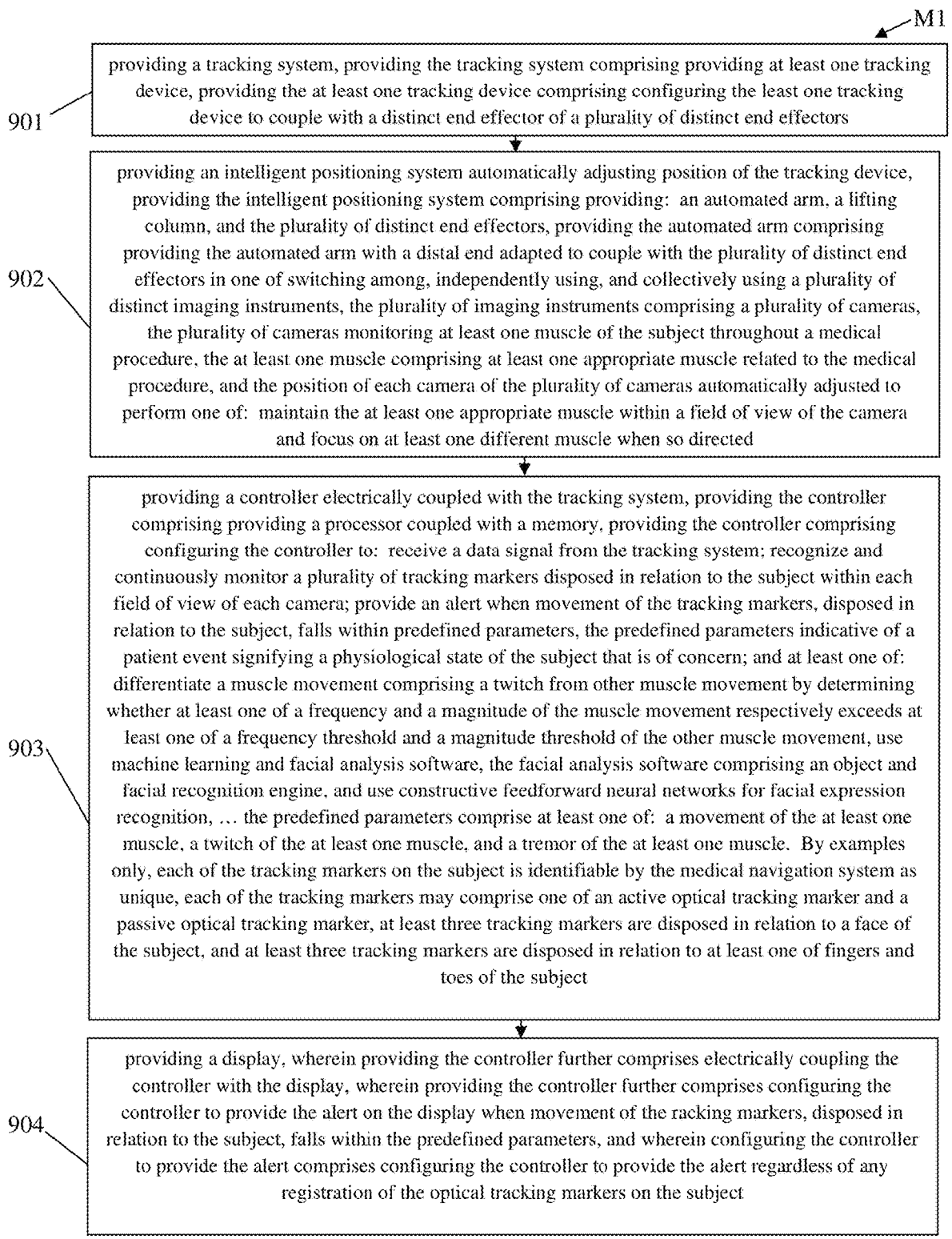
FIG. 9 is a flow chart illustrating a method of providing a medical navigation system for automatically detecting movement of a subject.

Referring to FIG. 9, this flow chart illustrates a method M1 of providing a medical navigation system for automatically detecting movement of a subject, in accordance with an embodiment of the present disclosure. The method M1 comprises: providing a tracking system, providing the tracking system comprising providing at least one tracking device, providing the at least one tracking device comprising configuring the least one tracking device to couple with a distinct end effector of a plurality of distinct end effectors, as indicated by block 901; providing an intelligent positioning system automatically adjusting position of the tracking device, providing the intelligent positioning system comprising providing: an automated arm, a lifting column, and the plurality of distinct end effectors, providing the automated arm comprising providing the automated arm with a distal end adapted to couple with the plurality of distinct end effectors in one of switching among, independently using, and collectively using a plurality of distinct imaging instruments, the plurality of imaging instruments comprising a plurality of cameras, the plurality of cameras monitoring at least one muscle of the subject throughout a medical procedure, the at least one muscle comprising at least one appropriate muscle related to the medical procedure, and the position of each camera of the plurality of cameras automatically adjusted to perform one of: maintain the at least one appropriate muscle within a field of view of the camera and focus on at least one different muscle when so directed, as indicated by block 902; and providing a controller electrically coupled with the tracking system, providing the controller comprising providing a processor coupled with a memory, providing the controller comprising configuring the controller to: receive a data signal from the tracking system; recognize and continuously monitor a plurality of tracking markers disposed in relation to the subject within each field of view of each camera; provide an alert when movement of the tracking markers, disposed in relation to the subject, falls within predefined parameters, the predefined parameters indicative of a patient event signifying a physiological state of the subject that is of concern; and at least one of: differentiate a muscle movement comprising a twitch from other muscle movement by determining whether at least one of a frequency and a magnitude of the muscle movement respectively exceeds at least one of a frequency threshold and a magnitude threshold of the other muscle movement, use machine learning and facial analysis software, the facial analysis software comprising an object and facial recognition engine, and use constructive feedforward neural networks for facial expression recognition, as indicated by block 903, whereby the intelligent positioning system, the tracking device, the automated arm, and the tracking markers, together, form a feedback loop, and whereby the feedback loop maintains a distal end of a port in constant view and in focus in relation to each distinct end effector.

Still referring to FIG. 9, in the method M1, the predefined parameters comprise at least one of: a movement of the at least one muscle, a twitch of the at least one muscle, and a tremor of the at least one muscle. By examples only, each of the tracking markers on the subject is identifiable by the medical navigation system as unique, each of the tracking markers may comprise one of an active optical tracking marker and a passive optical tracking marker, at least three tracking markers are disposed in relation to a face of the subject, and at least three tracking markers are disposed in relation to at least one of fingers and toes of the subject.

Still referring to FIG. 9, the method M1 further comprises providing a display, as indicated by block 904, wherein providing the controller further comprises electrically coupling the controller with the display, wherein providing the controller further comprises configuring the controller to provide the alert on the display when movement of the racking markers, disposed in relation to the subject, falls within the predefined parameters, and wherein configuring the controller to provide the alert comprises configuring the controller to provide the alert regardless of any registration of the optical tracking markers on the subject.

Figure 10:
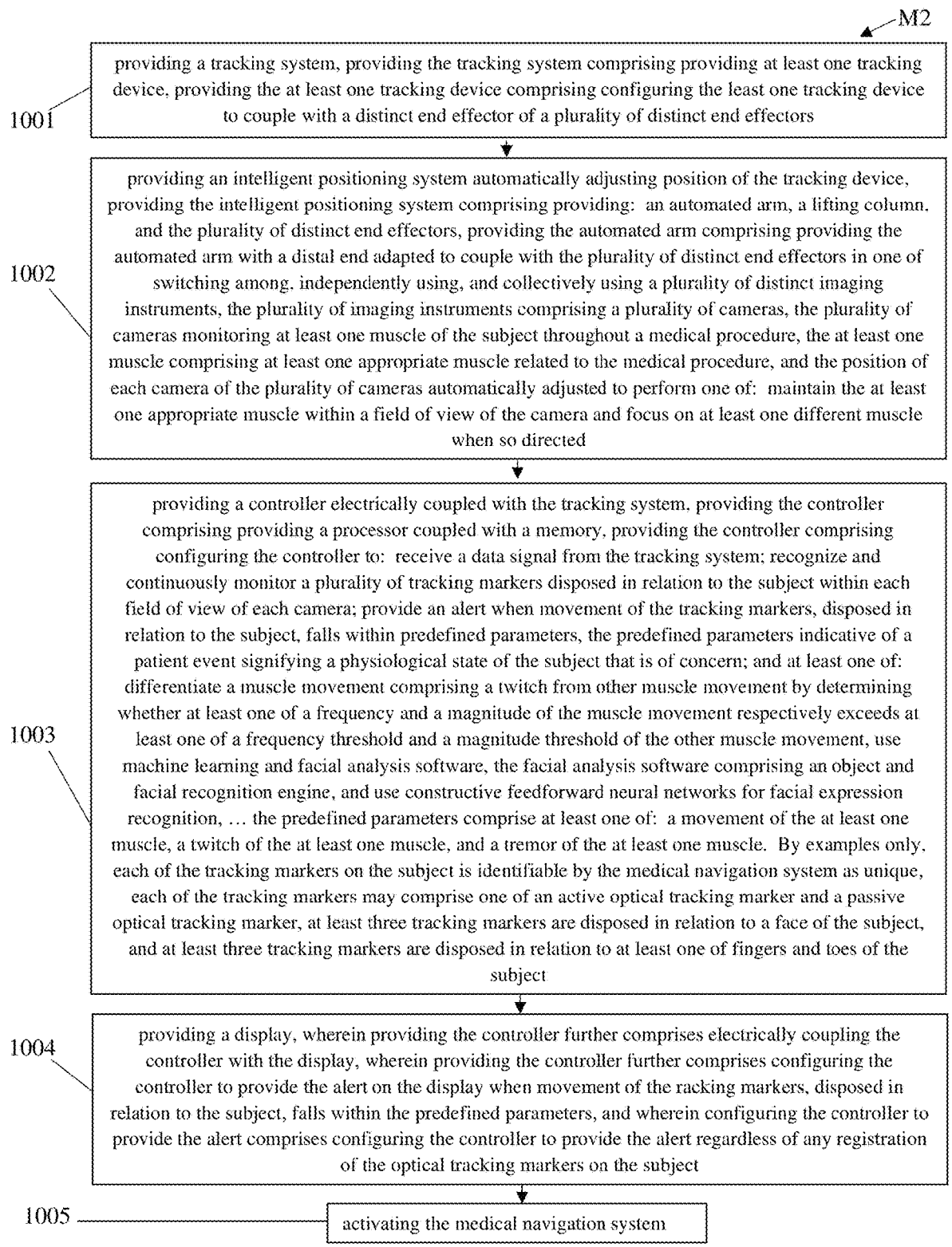
FIG. 10 is a flow chart illustrating a method of automatically detecting muscle movement implementable by way of a medical navigation system.

Referring to FIG. 10, this flow chart illustrates a method M2 of automatically detecting muscle movement implementable by way of a medical navigation system. The method M2 comprises: providing a tracking system, providing the tracking system comprising providing at least one tracking device, providing the at least one tracking device comprising configuring the least one tracking device to couple with a distinct end effector of a plurality of distinct end effectors, as indicated by block 1001; providing an intelligent positioning system automatically adjusting position of the tracking device, providing the intelligent positioning system comprising providing: an automated arm, a lifting column, and the plurality of distinct end effectors, providing the automated arm comprising providing the automated arm with a distal end adapted to couple with the plurality of distinct end effectors in one of switching among, independently using, and collectively using a plurality of distinct imaging instruments, the plurality of imaging instruments comprising a plurality of cameras, the plurality of cameras monitoring at least one muscle of the subject throughout a medical procedure, the at least one muscle comprising at least one appropriate muscle related to the medical procedure, and the position of each camera of the plurality of cameras automatically adjusted to perform one of: maintain the at least one appropriate muscle within a field of view of the camera and focus on at least one different muscle when so directed, as indicated by block 1002; and providing a controller electrically coupled with the tracking system, providing the controller comprising providing a processor coupled with a memory, providing the controller comprising configuring the controller to: receive a data signal from the tracking system; recognize and continuously monitor a plurality of tracking markers disposed in relation to the subject within each field of view of each camera; provide an alert when movement of the tracking markers, disposed in relation to the subject, falls within predefined parameters, the predefined parameters indicative of a patient event signifying a physiological state of the subject that is of concern; and at least one of: differentiate a muscle movement comprising a twitch from other muscle movement by determining whether at least one of a frequency and a magnitude of the muscle movement respectively exceeds at least one of a frequency threshold and a magnitude threshold of the other muscle movement, use machine learning and facial analysis software, the facial analysis software comprising an object and facial recognition engine, and use constructive feedforward neural networks for facial expression recognition, as indicated by block 1003, whereby the intelligent positioning system, the tracking device, the automated arm, and the tracking markers, together, form a feedback loop, and whereby the feedback loop maintains a distal end of a port in constant view and in focus in relation to each distinct end effector; and activating the medical navigation system, as indicated by block 1004.

Still referring to FIG. 10, in the method M2, the predefined parameters comprise at least one of: a movement of the at least one muscle, a twitch of the at least one muscle, and a tremor of the at least one muscle. By examples only, each of the tracking markers on the subject is identifiable by the medical navigation system as unique, each of the tracking markers may comprise one of an active optical tracking marker and a passive optical tracking marker, at least three tracking markers are disposed in relation to a face of the subject, and at least three tracking markers are disposed in relation to at least one of fingers and toes of the subject.

Still referring to FIG. 10, the method M2 further comprises providing a display, as indicated by block 1004, wherein providing the controller further comprises electrically coupling the controller with the display, wherein providing the controller further comprises configuring the controller to provide the alert on the display when movement of the racking markers, disposed in relation to the subject, falls within the predefined parameters, and wherein configuring the controller to provide the alert comprises configuring the controller to provide the alert regardless of any registration of the optical tracking markers on the subject. The method M2 further comprises activating the medical navigation system, as indicated by block 1005.

The specific embodiments described above have been shown by way of example, and understood is that these embodiments may be susceptible to various modifications and alternative forms. Further understood is that the claims are not intended to be limited to the particular forms disclosed, but rather to cover all modifications, equivalents, and alternatives falling within the spirit and scope of the present disclosure.

What is claimed:

1. A medical navigation system for automatically detecting movement of a subject, the system comprising:
   a tracking system, the tracking system comprising at least one tracking device, the at least one tracking device configured to couple with a distinct end effector of a plurality of distinct end effectors;
   an intelligent positioning system automatically adjusting position of the tracking device, the intelligent positioning system comprising an automated arm, a lifting column, and the plurality of distinct end effectors, the automated arm comprising a distal end adapted to couple with the plurality of distinct end effectors in one of switching among, independently using, and collectively using a plurality of distinct imaging instruments, the plurality of imaging instruments comprising a plurality of cameras, the plurality of cameras monitoring at least one muscle of the subject throughout a medical procedure, the at least one muscle comprising at least one appropriate muscle related to the medical procedure, and the position of each camera of the plurality of cameras automatically adjusted to perform one of: maintain the at least one appropriate muscle within a field of view of the camera and focus on at least one different muscle when so directed; and
   a controller electrically coupled with the tracking system, the controller comprising a processor coupled with a memory, the controller configured to:
   receive a data signal from the tracking system;
   recognize and continuously monitor a plurality of tracking markers disposed in relation to the subject within each field of view of each camera;

provide an alert when movement of the tracking markers, disposed in relation to the subject, falls within predefined parameters, the predefined parameters indicative of a patient event signifying a physiological state of the subject that is of concern; and at least one of: differentiate a muscle movement comprising a twitch from other muscle movement by determining whether at least one of a frequency and a magnitude of the muscle movement respectively exceeds at least one of a frequency threshold and a magnitude threshold of the other muscle movement, use machine learning and facial analysis software, the facial analysis software comprising an object and facial recognition engine, and use constructive feedforward neural networks for facial expression recognition, wherein the intelligent positioning system, the tracking device, the automated arm, and the tracking markers form a feedback loop, and wherein the feedback loop maintains a distal end of a port in constant view and in focus in relation to each distinct end effector.

2. The system of claim 1, wherein the predefined parameters comprise at least one of: a movement of the at least one muscle, a twitch of the at least one muscle, and a tremor of the at least one muscle.

3. The system of claim 1, wherein each of the tracking markers on the subject is identifiable by the medical navigation system as unique.

4. The system of claim 1, wherein each of the tracking markers comprises one of an active optical tracking marker and a passive optical tracking marker.

5. The system of claim 1, wherein at least three tracking markers are disposed in relation to a face of the subject.

6. The system of claim 1, wherein at least three tracking markers are disposed in relation to at least one of fingers and toes of the subject.

7. The system of claim 1, further comprising a display, wherein the controller is further electrically coupled with the display, wherein the controller is further configured to provide the alert on the display when movement of the racking markers, disposed in relation to the subject, falls within the predefined parameters, and wherein the alert is provided regardless of any registration of the optical tracking markers on the subject.

8. A method of providing a medical navigation system for automatically detecting movement of a subject, the method comprising:

providing a tracking system, providing the tracking system comprising providing at least one tracking device, providing the at least one tracking device comprising configuring the least one tracking device to couple with a distinct end effector of a plurality of distinct end effectors;

providing an intelligent positioning system automatically adjusting position of the tracking device, providing the intelligent positioning system comprising providing: an automated arm, a lifting column, and the plurality of distinct end effectors, providing the automated arm comprising providing the automated arm with a distal end adapted to couple with the plurality of distinct end effectors in one of switching among, independently using, and collectively using a plurality of distinct imaging instruments, the plurality of imaging instruments comprising a plurality of cameras, the plurality of cameras monitoring at least one muscle of the subject throughout a medical procedure, the at least one muscle comprising at least one appropriate muscle related to the medical procedure, and the position of each camera of the plurality of cameras automatically adjusted to perform one of: maintain the at least one appropriate muscle within a field of view of the camera and focus on at least one different muscle when so directed; and providing a controller electrically coupled with the tracking system, providing the controller comprising providing a processor coupled with a memory, providing the controller comprising configuring the controller to:

receive a data signal from the tracking system;

recognize and continuously monitor a plurality of tracking markers disposed in relation to the subject within each field of view of each camera;

provide an alert when movement of the tracking markers, disposed in relation to the subject, falls within predefined parameters, the predefined parameters indicative of a patient event signifying a physiological state of the subject that is of concern; and at least one of: differentiate a muscle movement comprising a twitch from other muscle movement by determining whether at least one of a frequency and a magnitude of the muscle movement respectively exceeds at least one of a frequency threshold and a magnitude threshold of the other muscle movement, use machine learning and facial analysis software, the facial analysis software comprising an object and facial recognition engine, and use constructive feedforward neural networks for facial expression recognition, whereby the intelligent positioning system, the tracking device, the automated arm, and the tracking markers, together, form a feedback loop, and whereby the feedback loop maintains a distal end of a port in constant view and in focus in relation to each distinct end effector.

9. The method of claim 8, wherein the predefined parameters comprise at least one of: a movement of the at least one muscle, a twitch of the at least one muscle, and a tremor of the at least one muscle.

10. The method of claim 8, wherein each of the tracking markers on the subject is identifiable by the medical navigation system as unique.

11. The method of claim 8, wherein each of the tracking markers comprises one of an active optical tracking marker and a passive optical tracking marker.

12. The method of claim 8, wherein at least three tracking markers are disposed in relation to a face of the subject.

13. The method of claim 8, wherein at least three tracking markers are disposed in relation to at least one of fingers and toes of the subject.

14. The method of claim 8, further comprising providing a display, wherein providing the controller further comprises electrically coupling the controller with the display wherein providing the controller further comprises configuring the controller to provide the alert on the display when movement of the racking markers, disposed in relation to the subject, falls within the predefined parameters, and wherein configuring the controller to provide the alert comprises configuring the controller to provide the alert regardless of any registration of the optical tracking markers on the subject.

15. A method of automatically detecting movement of a subject by way of a medical navigation system, the method comprising:

providing the medical navigation system, providing the medical navigation system comprising:

providing a tracking system, providing the tracking system comprising providing at least one tracking device, providing the at least one tracking device comprising configuring the least one tracking device to couple with a distinct end effector of a plurality of distinct end effectors;

providing an intelligent positioning system automatically adjusting position of the tracking device, providing the intelligent positioning system comprising providing: an automated arm, a lifting column, and the plurality of distinct end effectors, providing the automated arm comprising providing the automated arm with a distal end adapted to couple with the plurality of distinct end effectors in one of switching among, independently using, and collectively using a plurality of distinct imaging instruments, the plurality of imaging instruments comprising a plurality of cameras, the plurality of cameras monitoring at least one muscle of the subject throughout a medical procedure, the at least one muscle comprising at least one appropriate muscle related to the medical procedure, and the position of each camera of the plurality of cameras automatically adjusted to perform one of maintain the at least one appropriate muscle within a field of view of the camera and focus on at least one different muscle when so directed; and providing a controller electrically coupled with the tracking system, providing the controller comprising providing a processor coupled with a memory, providing the controller comprising configuring the controller to:

receive a data signal from the tracking system;

recognize and continuously monitor a plurality of tracking markers disposed in relation to the subject within each field of view of each camera;

provide an alert when movement of the tracking markers, disposed in relation to the subject, falls within predefined parameters, the predefined parameters indicative of a patient event signifying a physiological state of the subject that is of concern; and at least one of: differentiate a muscle movement comprising a twitch from other muscle movement by determining whether at least one of a frequency and a magnitude of the muscle movement respectively exceeds at least one of a frequency threshold and a magnitude threshold of the other muscle movement, use machine learning and facial analysis software, the facial analysis software comprising an object and facial recognition engine, and use constructive feed-forward neural networks for facial expression recognition, whereby the intelligent positioning system, the tracking device, the automated arm, and the tracking markers, together, form a feedback loop, and whereby the feedback loop maintains a distal end of a port in constant view and in focus in relation to each distinct end effector; and activating the medical navigation system.

16. The method of claim 15, wherein the predefined parameters comprise at least one of: a movement of the at least one muscle, a twitch of the at least one muscle, and a tremor of the at least one muscle.

17. The method of claim 15, wherein each of the tracking markers on the subject is identifiable by the medical navigation system as unique.

18. The method of claim 16, wherein each of the tracking markers comprises one of an active optical tracking marker and a passive optical tracking marker.

19. The method of claim 15, wherein one of: at least three tracking markers are disposed in relation to a face of the subject, and at least three tracking markers are disposed in relation to at least one of fingers and toes of the subject.

20. The method of claim 15, further comprising providing a display, wherein providing the controller further comprises electrically coupling the controller with the display, wherein providing the controller further comprises configuring the controller to provide the alert on the display when movement of the racking markers, disposed in relation to the subject, falls within the predefined parameters, and wherein configuring the controller to provide the alert comprises configuring the controller to provide the alert regardless of any registration of the optical tracking markers on the subject.

* * * * *